US008116555B2

(12) United States Patent
Ahn et al.

(10) Patent No.: US 8,116,555 B2
(45) Date of Patent: Feb. 14, 2012

(54) VISION INSPECTION SYSTEM AND METHOD FOR INSPECTING WORKPIECE USING THE SAME

(75) Inventors: Woo Jung Ahn, Seongnam Si (KR); Jung Hwan Kim, Seoul (KR); Hee Wook You, Seoul (KR)

(73) Assignee: SNU Precision Co., Ltd., Seoul (KR)

( * ) Notice: Subject to any disclaimer, the term of this patent is extended or adjusted under 35 U.S.C. 154(b) by 674 days.

(21) Appl. No.: 12/266,437

(22) Filed: Nov. 6, 2008

(65) Prior Publication Data

US 2009/0087080 A1 Apr. 2, 2009

Related U.S. Application Data

(63) Continuation of application No. PCT/KR2007/003337, filed on Jul. 10, 2007.

(30) Foreign Application Priority Data

Mar. 28, 2007 (KR) .................. 10-2007-0030469

(51) Int. Cl.
*G06K 9/00* (2006.01)
(52) U.S. Cl. ...................................... 382/141
(58) Field of Classification Search .................. 382/141
See application file for complete search history.

(56) References Cited

U.S. PATENT DOCUMENTS

| 6,081,981 | A | 7/2000 | Demarest et al. |
| 6,180,914 | B1 | 1/2001 | Jones et al. |
| 6,483,935 | B1* | 11/2002 | Rostami et al. ............... 382/141 |
| 7,030,351 | B2 | 4/2006 | Wasserman et al. |
| 2003/0197925 | A1 | 10/2003 | Hamborg |

FOREIGN PATENT DOCUMENTS

| JP | 11-264803 A | 9/1999 |
| JP | 2000-131245 A | 5/2000 |
| JP | 2001-41905 A | 2/2001 |
| JP | 2005-164558 A | 6/2005 |
| JP | 2006-194755 A | 7/2006 |
| KR | 10-2005-0061752 | 6/2005 |

OTHER PUBLICATIONS

International Search Report dated Dec. 26, 2007.
Office Action dated Nov. 9, 2010 from the Japanese Patent Office in the counterpart Japanese Patent Application No. 2009-506426.

* cited by examiner

*Primary Examiner* — Roy M Punnoose
(74) *Attorney, Agent, or Firm* — Knobbe Martens Olson & Bear LLP (57) ABSTRACT

A vision inspection system and a workpiece inspection method are used in inspecting a workpiece. The vision inspection system includes a level block having an upper surface whose opposite end regions are defined as a first position and a second position. A first transfer device has a table for supporting the workpiece. The first transfer device is installed on the upper surface of the level block for rectilinearly moving the table between the first position and the second position. A camera is arranged above the level block for taking an image of the workpiece to output image data. A second transfer device is installed on the upper surface of the level block for rectilinearly moving the camera between the first position and the second position. A computer is connected to the first transfer means, the camera and the second transfer means to control them in a specified manner.

18 Claims, 5 Drawing Sheets

A: Relative Displacement of Table and Camera
B: Vertical Vibratory Displacement of Level Block

FIG.5

A: Relative Displacement of Table and Camera
B: Vertical Vibratory Displacement of Level Block

FIG.6

VISION INSPECTION SYSTEM AND METHOD FOR INSPECTING WORKPIECE USING THE SAME

CROSS-REFERENCE TO RELATED APPLICATIONS

This application is a continuation application under 35 U.S.C. §365(c) of International Application No. PCT/KR2007/003337, filed on Jul. 10, 2007 designating the United States of America and published in the English language. This application further claims the benefit of the earlier filing dates under 35 U.S.C. §365(b) of Korean Patent Application No. 10-2007-0030469, filed on Mar. 28, 2007. This application incorporates herein by reference the International Application No. PCT/KR2007/003337 and the Korean Patent Application No. 10-2007-0030469 in their entirety.

BACKGROUND

1. Field

The present disclosure relates to a vision inspection system and a method for inspecting a workpiece using the same and, more particularly, to a vision inspection system for acquiring and inspecting image data of a workpiece and a method for inspecting a workpiece using the same.

2. Description of the Related Technology

A vision inspection system includes a camera for taking images of various objects to acquire image data and a computer for processing the image data inputted from the camera using an image processing program. The vision inspection system finds its application in a variety of fields, including object identification, object inspection, object measurement and assortment of accepted and rejected products.

Vision inspection systems are disclosed in U.S. Pat. No. 7,030,351, U.S. Patent Publication No. 2003/0197925A1 and many other patent documents. The vision inspection systems disclosed in these patent documents are formed of a workpiece stage, a camera stage, a controller, a camera and a computer. For the purpose of loading, unloading and positioning a workpiece, the workpiece stage is designed to make rectilinear movement in X-axis and Y-axis directions. The camera stage is arranged above the workpiece stage. For the sake of positioning and focusing the camera, the camera stage is configured to make rectilinear movement in X-axis, Y-axis and Z-axis directions and rotational movement about the Z-axis. The computer is connected to the computer so that it can control the operation of the workpiece stage and the camera stage.

The vision inspection systems taught in the above-cited patent documents suffer from generation of severe errors, because the image data are acquired by fixing one of the workpiece or the camera and moving the other. In the event that the camera is repeatedly moved and stopped to take images of the workpiece while the workpiece is fixed in place, a great deal of vibration is generated in the vision inspection systems, which in turn increases the errors of the image data. Another drawback is that it is time-consuming to take images of the workpiece by repeatedly moving and stopping the camera relative to the fixed workpiece.

In case the camera is fixed in place and the images of the workpiece are taken by moving the workpiece relative to the fixed camera, there is a problem in that the vibration generated during the workpiece movement greatly reduces the reliability of the image data and the task of taking images of the workpiece is time-consuming. Particularly, the vision inspection systems taught in the above-cited patent documents are unsuitable for use in accurately inspecting and measuring large-size workpieces such as a glass substrate, a cell and a module, which forms a flat display such as a TFT-LCD (Thin Film Transistor-Liquid Crystal Display), a PDP (Plasma Display Panel) or an EL (Electroluminescent) Display.

The foregoing discussion is to provide background information of the invention and does not constitute an admission of prior art.

SUMMARY

One aspect of the present disclosure provides a method of visual inspection of an object. The method comprises moving an inspection object in a first direction, moving a camera in a second direction opposite to the first direction, capturing at least one image of the object using the camera, and processing the at least one image of the object.

In one embodiment, moving of the camera can be controlled such that a first torque generated by moving of the camera substantially compensates a second torque generated by moving of the object. The second torque can vary depending on acceleration or deceleration of the object and a mass of the object. The first torque can vary depending on acceleration or deceleration of the camera and a mass of the camera. The method can further include controlling acceleration or deceleration of the object during moving. The method can further include controlling acceleration or deceleration of the camera during moving. The method can further comprise controlling acceleration or deceleration of at least one of the object and the camera during moving thereof, wherein the first torque is proportional to a first distance between the camera and a reference point in a third direction perpendicular to the first direction and the second torque is proportional to a second distance between the object and the reference point in the third direction.

In one embodiment, capturing the at least one image of the object occurs when the camera and the object are stopped after moving opposite directions. In another embodiment of the method, wherein capturing the at least one image of the object occurs when the camera and the object are aligned with each other. In one embodiment, the inspection object comprises a flat panel display device. In one embodiment, processing comprises identifying the object from the at least one image. In another embodiment, processing comprises inspecting the object on the at least one image. Processing can further include determining whether to accept or reject the object based on processing.

One embodiment of the present disclosure provides a visual inspection system. The system comprises a table slidable in a first direction and configured to place an inspection object on, a camera slidable in a second direction opposite to the first direction and configured to capture images of the object, and a computing device configured to process at least one image of the object captured by the camera and to identify a defect on the object. In one embodiment, the system is configured so as to control sliding of the table and the camera in a manner that a torque generated by sliding of the camera substantially compensates a torque generated by sliding of the table.

In one embodiment, the system can further comprise a level block supporting the table and the camera. The system can further comprise a plurality of base isolators for supporting the level block. In one embodiment, the table is slidable on an upper surface of the level block straight in the first direction. In another embodiment, the camera is slidable on the upper surface of the level block straight in the second direction. In one embodiment, the system can comprise a plurality of cameras with each camera configured to capture at least one image of a portion of the object.

One aspect of the present disclosure, there is provided a vision inspection system comprising: a level block having an upper surface whose opposite end regions are defined as a first position and a second position; a first transfer means having a table for supporting a workpiece, the first transfer means installed on the upper surface of the level block for rectilinearly moving the table between the first position and the second position; a camera arranged above the level block for taking an image of the workpiece to output image data; a second transfer means installed on the upper surface of the level block for rectilinearly moving the camera between the first position and the second position; and a computer connected to the first transfer means, the camera and the second transfer means, the computer designed to control the first transfer means in such a manner as to move the table from the first position toward the second position and also to control the second transfer means in such a manner as to move the cameras from the second position toward the first position, the computer provided with an image processing program for processing the image data inputted from the camera.

Another aspect of the present disclosure, there is provided a method for inspecting a workpiece using a vision inspection system, the vision inspection system including a level block having an upper surface whose opposite end regions are defined as a first position and a second position, a first transfer means installed on the upper surface of the level block and provided with a table capable of making rectilinear movement between the first position and the second position, at least one camera arranged above the level block, a second transfer means installed on the upper surface of the level block for rectilinearly moving the camera between the first position and the second position, and a computer for processing image data inputted from the camera, the method comprising the steps of: causing the first transfer means to bring the table into the first position; loading the workpiece onto the table kept in the first position; causing the second transfer means to bring the camera into the second position; causing the first transfer means to move the table from the first position toward the second position, while causing the second transfer means to move the camera from the second position toward the first position; acquiring image data of the workpiece by causing the camera to take an image of the workpiece; and causing the computer to process the image data inputted from the camera.

An aspect of the present disclosure to provides a vision inspection system capable of acquiring image data by moving a workpiece and a camera toward each other, consequently minimizing the torque exerted in the system as a whole and greatly enhancing the reliability of the acquired image data, and a method for inspecting a workpiece using the same.

Another aspect of the present disclosure is to provide a vision inspection system capable of shortening the time required in inspecting a workpiece and a method for inspecting a workpiece using the same.

BRIEF DESCRIPTION OF THE DRAWINGS

The above and other features of the present disclosure will become apparent from the following description of preferred embodiments, given in conjunction with the accompanying drawings, in which.

DETAILED DESCRIPTION OF EMBODIMENT

Various embodiments in accordance with the present invention will now be described in detail with reference to the accompanying drawings.

Figure 1:
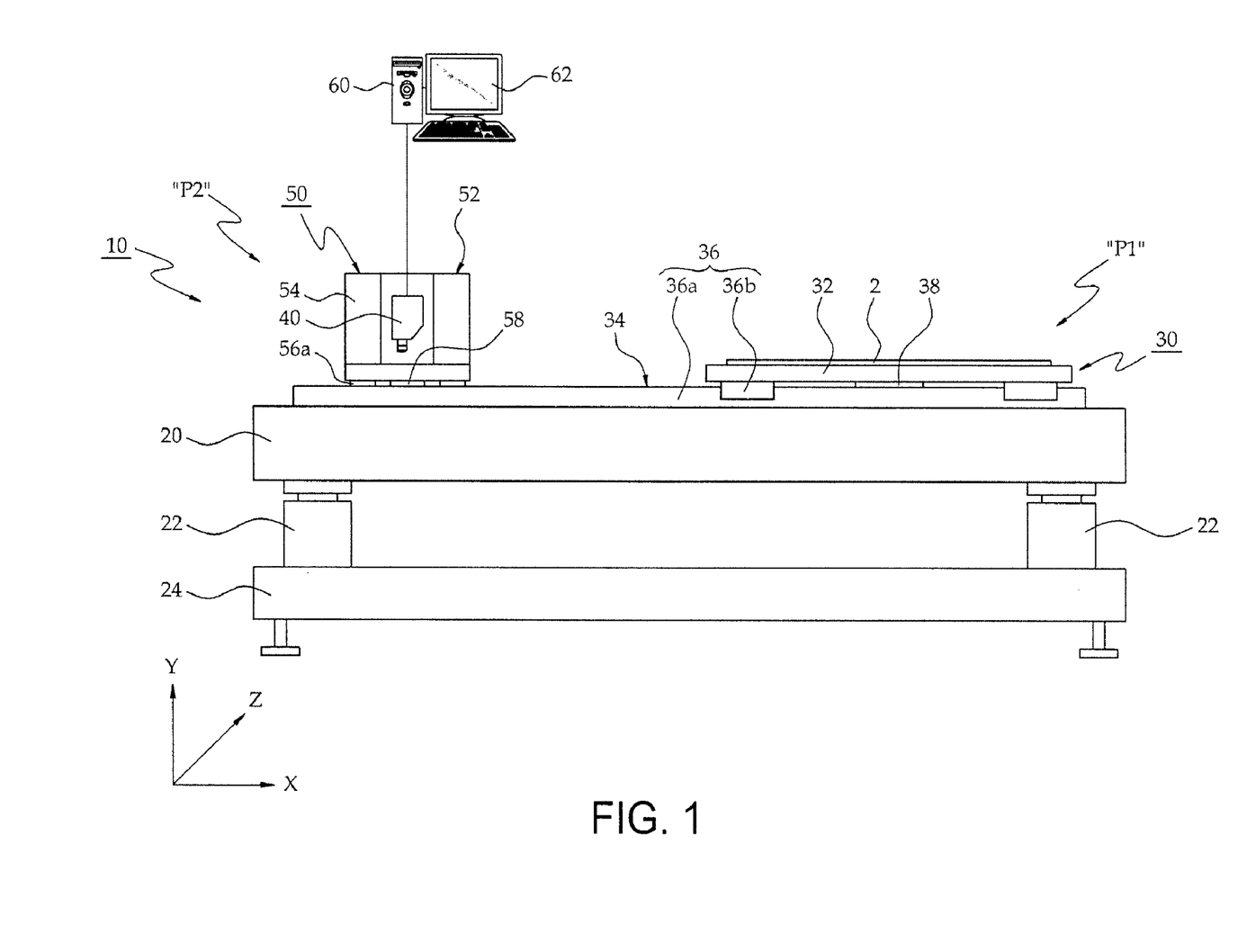
FIG. 1 is a front view showing a vision inspection system in accordance with one embodiment of the present invention.
Figure 2:
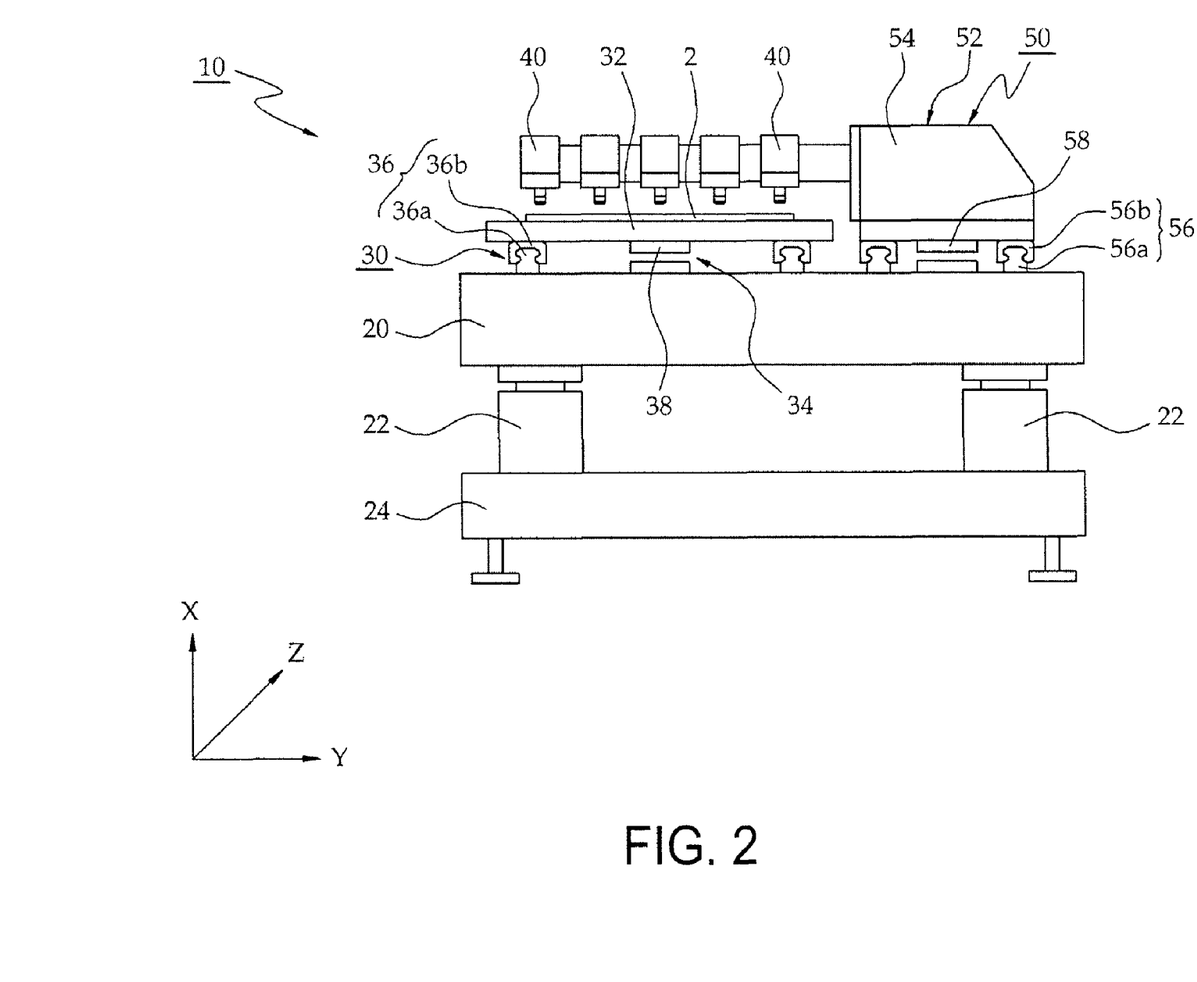
FIG. 2 is a side view showing the vision inspection system in accordance with one embodiment of the present invention.

Referring first to FIGS. 1 and 2, a vision inspection system 10 of the present disclosure is designed to inspect and measure defects existing in a workpiece 2 or an inspection object such as a glass substrate, a cell and a module, which forms a flat display. The vision inspection system 10 includes a level block 20 having an upper surface accurately and smoothly machined in an effort to assure accurate inspection and measurement of the workpiece 2. The opposite end regions on the upper surface of the level block 20 are defined as a first position P1 and a second position P2, respectively. Although the first position P1 and the second position P2 are arranged along an X-axis direction of the level block 20 in FIGS. 1 and 2, they may be arranged along a Y-axis direction of the level block 20. The level block 20 is stably supported on an upper surface of a base 24 by a plurality of base isolators 22 that absorb shock and vibration.

On the upper surface of the level block 20, there is provided a first transfer device 30 for transferring the workpiece 2 between the first position P1 and the second position P2. The first transfer device 30 is formed of a table 32 and a linear actuator 34. The table 32 is arranged above the level block 20 so that it can be moved between the first position P1 and the second position P2. The workpiece 2 is placed on the table 32.

The linear actuator 34 is mounted between the upper surface of the level block 20 and the lower surface of the table 32. The linear actuator 34 causes the table 32 to make rectilinear reciprocating movement between the first position P1 and the second position P2. The linear actuator 34 includes a pair of linear motion guides 36 mounted between the upper surface of the level block 20 and the lower surface of the table 32 and a linear motor 38 arranged between the linear motion guides 36 and operatively connected to the table 32. Each of the linear motion guides 36 includes a guide rail 36a fixed to the upper surface of the level block 20, the guide rail 36a extending across the first position P1 and the second position P2, and a plurality of sliders 36b slidably mounted to the guide rail 36a and fixed to the lower surface of the table 32. The table 32 is rectilinearly moved between the first position P1 and the second position P2 by the driving power of the linear motor 38 and under the guidance of the linear motion guides 36.

Alternatively, the linear actuator 34 may include a servo motor, a lead screw, a ball nut and a pair of linear motion guides. The first transfer device 30 may be formed of an orthogonal coordinate robot that includes an X-axis actuator and a Y-axis actuator for rectilinearly reciprocating the table 32 in the X-axis and Y-axis directions of the level block 20. Furthermore, the first transfer device 30 may be formed of a multi-axis robot capable of rectilinearly reciprocating the table 32 in the X-axis, Y-axis and Z-axis directions of the level block 20 and also capable of rotating and tilting the table 32 about one of the X-axis, Y-axis and Z-axis. The workpiece 2 may be accurately positioned on the table 32 by using the orthogonal coordinate robot or the multi-axis robot.

Cameras 40 are arranged above the level block 20 for movement between the first position P1 and the second position P2. The cameras 40 serve to output image data by taking images of the workpiece 2. Each of the cameras 40 may be formed of a charged coupled device camera. Although five cameras 40 are arranged along the Y-axis direction of the level block 20 in FIG. 2, the number and arrangement positions of the cameras 40 may be arbitrarily changed depending on the circumstances.

Figure 3:
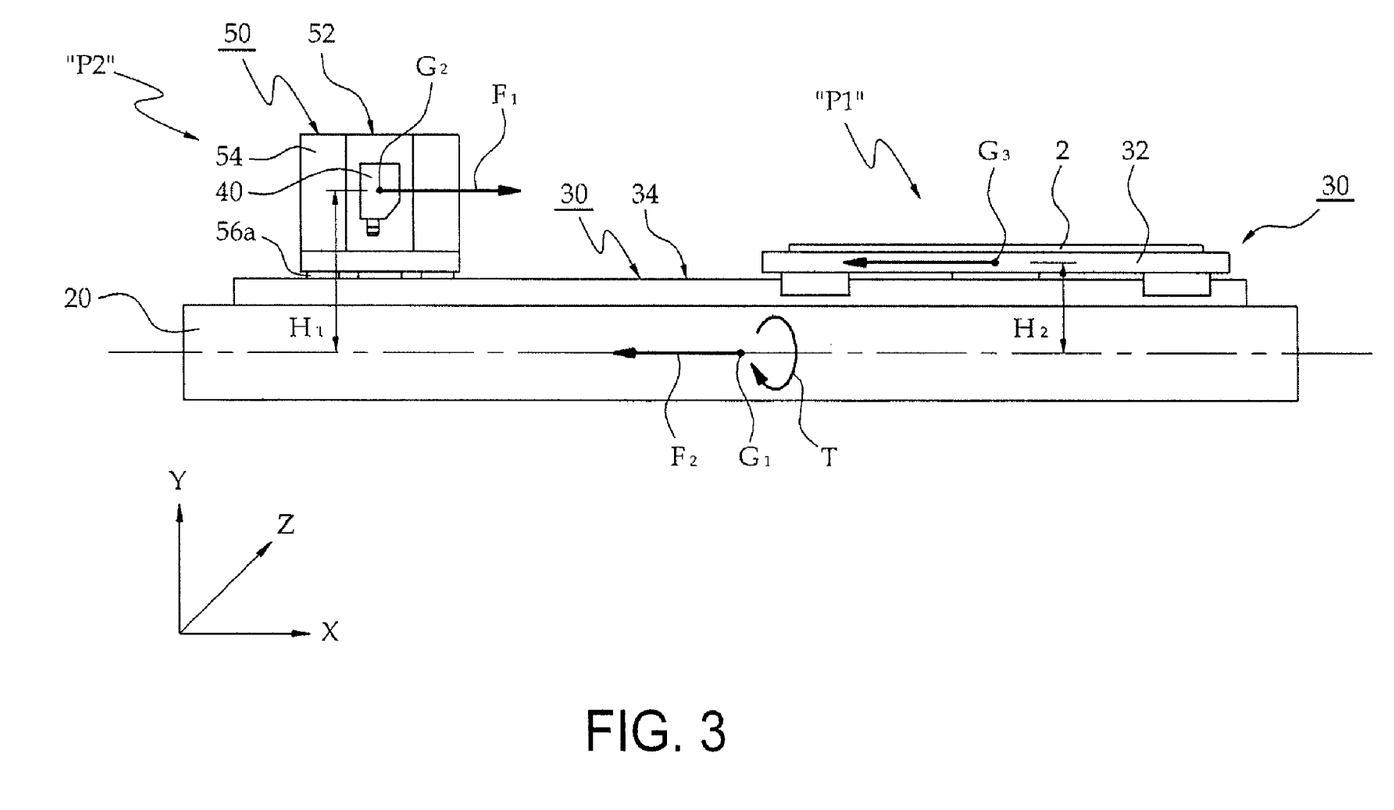
FIG. 3 is a schematic front view illustrating the operation of the vision inspection system in accordance with one embodiment of the present invention.

Referring to FIGS. 1 and 3, the vision inspection system 10 includes a second transfer device 50 installed on the upper surface of the level block 20 so that it can transfer the cameras 40 from the second position P2 toward the first position P1. The second transfer device 50 is formed of a linear actuator 52 that can transfer the cameras 40 in a direction opposite to the movement direction of the workpiece 2. The linear actuator 52 includes a carriage 54, a pair of linear motion guides 56 and a linear motor 58.

The carriage 54 is arranged above the level block 20 so that it can move between the first position P1 and the second position P2. The cameras 40 are attached to the carriage 54. The linear motion guides 56 are arranged between the upper surface of the level block 20 and the lower surface of the carriage 54 in a parallel relationship with each other so that they can guide rectilinear movement of the carriage 54. The linear motor 58 is mounted between the linear motion guides 56 so that it can cause the carriage 54 to move along the linear motion guides 56. Each of the linear motion guides 56 includes a guide rail 56a fixed to the upper surface of the level block 20, the guide rail 36a extending across the first position P1 and the second position P2, and a plurality of sliders 56b slidably mounted to the guide rail 56a and fixed to the lower surface of the carriage 54. Just like the linear actuator 34 of the first transfer device 30, the linear actuator 52 of the second transfer device 50 may be formed of an orthogonal coordinate robot or a multi-axis robot. In order to perform fine positioning and focusing tasks, the cameras 40 may be attached to a stage which in turn is mounted to the carriage 54.

Turning back to FIG. 1, the vision inspection system 10 includes a computer 60 connected to the linear motor 38 of the first transfer device 30, the cameras 40 and the linear motor 58 of the second transfer device 50. The computer 60 serves to control the operation of the first transfer device 30, the cameras 40 and the second transfer device 50. The computer 60 controls the operation of the first transfer device 30 in such a manner as to transfer the workpiece 2 placed on the table 32 from the first position P1 to the second position P2 and also controls the operation of the second transfer device 50 to transfer the cameras 40 attached to the carriage 54 from the second position P2 to the first position P1. Furthermore, the computer 60 is designed to process the image data inputted from the cameras 40 by use of an image processing program. The image data of the workpiece 2 thus acquired is outputted to a monitor 62 or other display devices.

Figure 6:
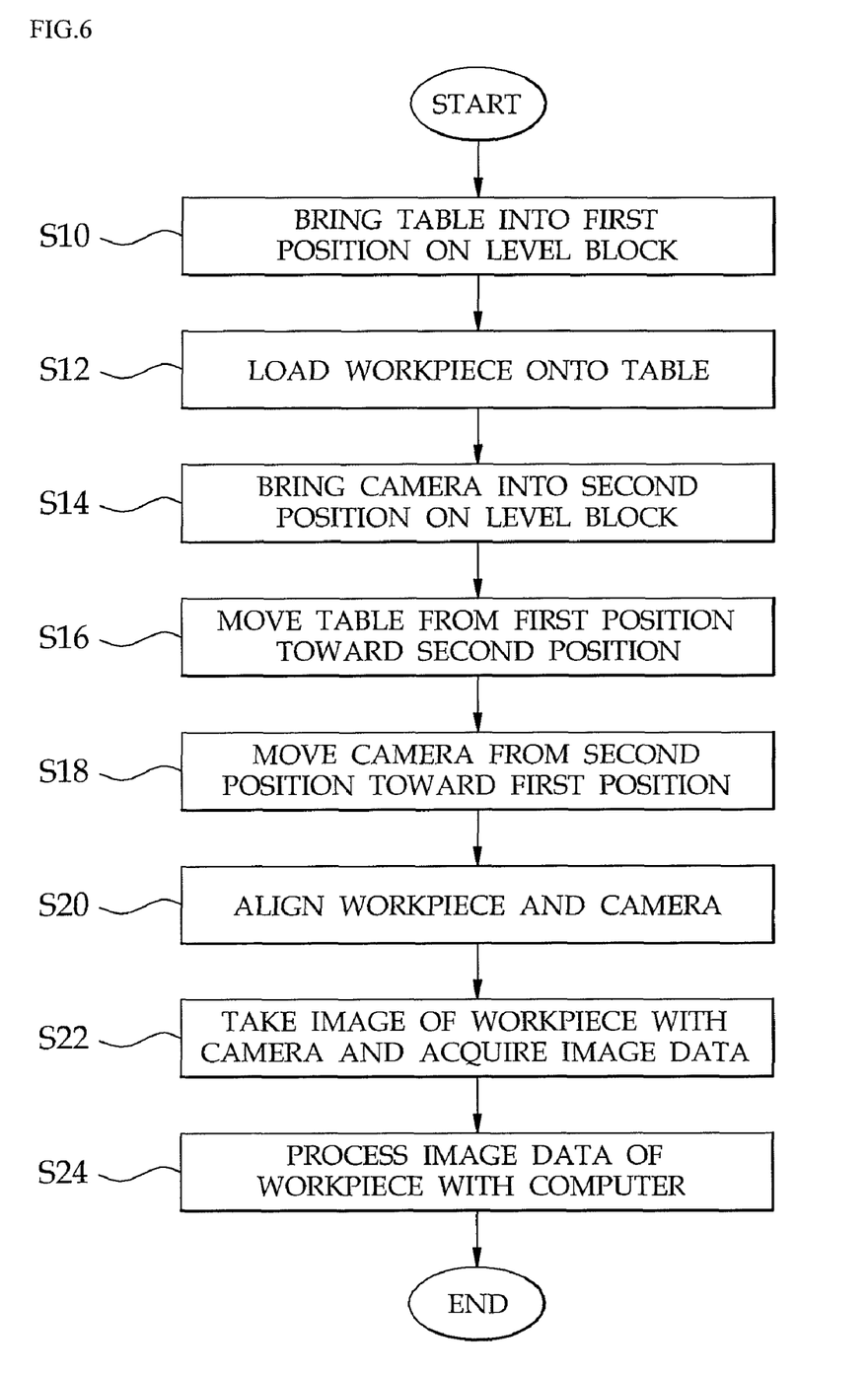
FIG. 6 is a flowchart for explaining a workpiece inspection method in accordance with one embodiment of the present invention.

Now, a workpiece inspection method using the vision inspection system of the above configuration will be described with reference to FIG. 6.

Referring collectively to FIGS. 1 and 2, the table 32 is brought into the first position P1 on the level block 20 by operating the linear actuator 34 (S10). Then, the workpiece 2 is loaded onto the table 32 (S12). The tasks of loading and unloading the workpiece 2 may be conducted by a transfer feeder, a handler, a conveyor or other devices.

Next, the cameras 40 are brought into the second position P2 on the level block 20 by operating the linear actuator 52 (S14). Once the workpiece 2 is loaded and the cameras 40 are positioned in place, the computer 60 controls the operation of the first transfer device 30 in such a manner as to move the table 32 from the first position P1 toward the second position P2 (S16). The linear motor 38 of the linear actuator 34 is driven under the control of the computer 60, whereby the table 32 is transferred from the first position P1 to the second position P2. At this time, the rectilinear movement of the table 32 is guided by the linear motion guides 36.

At the same moment when the table 32 is transferred by the first transfer device 30, the computer 60 controls the operation of the second transfer device 50 in such a manner as to transfer the carriage 54 from the second position P2 to the first position P1 (S18). As the linear motor 58 of the linear actuator 52 is driven under the control of the computer 60, the carriage 54 is transferred from the second position P2 to the first position P1. At this time, the rectilinear movement of the carriage 54 is guided by the linear motion guides 56. As a result, the cameras 40 are moved in a direction opposite to the movement direction of the workpiece 2 so that the workpiece 2 and the cameras 40 can move toward each other.

The computer 60 controls the operation of the first transfer device 30 and the second transfer device 50 in such a manner as to ensure that the workpiece 2 placed on the table 32 comes into alignment with the cameras 40 attached to the carriage 54 of the second transfer device 50 (S20). Once the cameras 40 are aligned in a position for inspection of the workpiece 2, the linear motor 38 of the first transfer device 30 and the linear motor 58 of the second transfer device 50 are stopped under the control of the computer 60.

Referring to FIG. 3, the second transfer device 50 is decelerated to a zero speed or accelerated from the zero speed during its movement on the upper surface of the level block 20. At this time, the force $F_1$ acting at the gravity center $G_2$ of the second transfer device 50 is represented by the equation: $F_1 = m_1 \times a_1$, where $m_1$ is the mass of the second transfer device 50 and $a_1$ is the acceleration of the second transfer device 50. A reaction force $F_2$ and a reaction torque T are acting against the force $F_1$ at the gravity center $G_1$ of the vision inspection system 10.

Assuming that the base isolators 22 hold the level block 20 against any rotation, the workpiece 2 is transferred from the first position P1 to the second position P2 by the first transfer device 30. In concert with the movement of the workpiece 2, the cameras 40 are transferred by the second transfer device 50 in a direction opposite to the movement direction of the workpiece 2. Since the first transfer device 30 and the second transfer device 50 are moved in the opposite directions, the reaction force and the reaction torque acting in the vision inspection system 10 are cancelled with each other. This reduces the force and the torque acting at the gravity center $G_1$ of the vision inspection system 10.

The ratio of the acceleration $a_1$ of the second transfer device 50 to the acceleration $a_2$ of the table 32, which can minimize the torque acting at the gravity center $G_1$ of the vision inspection system 10, is found by the equation: $m_1 \times a_1 \times h_1 = m_2 \times a_2 \times h_2$, where $h_1$ is the height between the gravity center $G_1$ of the vision inspection system 10 and the gravity center $G_2$ of the second transfer device 50, $m_2$ is the mass of the table 32 and $h_2$ is the height between the gravity center $G_1$ of the vision inspection system 10 and the gravity center $G_3$ of the table 32. If the acceleration $a_2$ of the table 32 and the acceleration $a_1$ of the second transfer device 50 are servile to the ratio of $a_1:a_2$, the torque acting at the gravity center $G_1$ of the vision inspection system 10 is minimized.

Experiments in an Example and a Comparative Example were conducted through the use of the vision inspection system 10 to confirm whether the torque of the vision inspection system 10 is reduced as the cameras 40 are transferred at the ratio of $a_1:a_2$ in a direction opposite to the movement direction of the workpiece 2. In the experiment of the Example, the cameras 40 were transferred at the ratio of $a_1:a_2$ in a direction opposite to the movement direction of the workpiece 2 so that the workpiece 2 and the cameras 40 can move toward each other. In the experiment of the Comparative Example, only the cameras 40 were transferred in a state that the workpiece 2 is fixed in place.

In the experiments of the Example and the Comparative Example, the relative displacement of the table 32 and the cameras 40 was measured by a capacitance sensor. The vertical vibratory displacement of the level block 20 was measured by a laser displacement sensor. The results of experiments in the Example are shown in FIG. 4, while the results of experiments in the Comparative Example are shown in FIG. 5.

Figure 4:
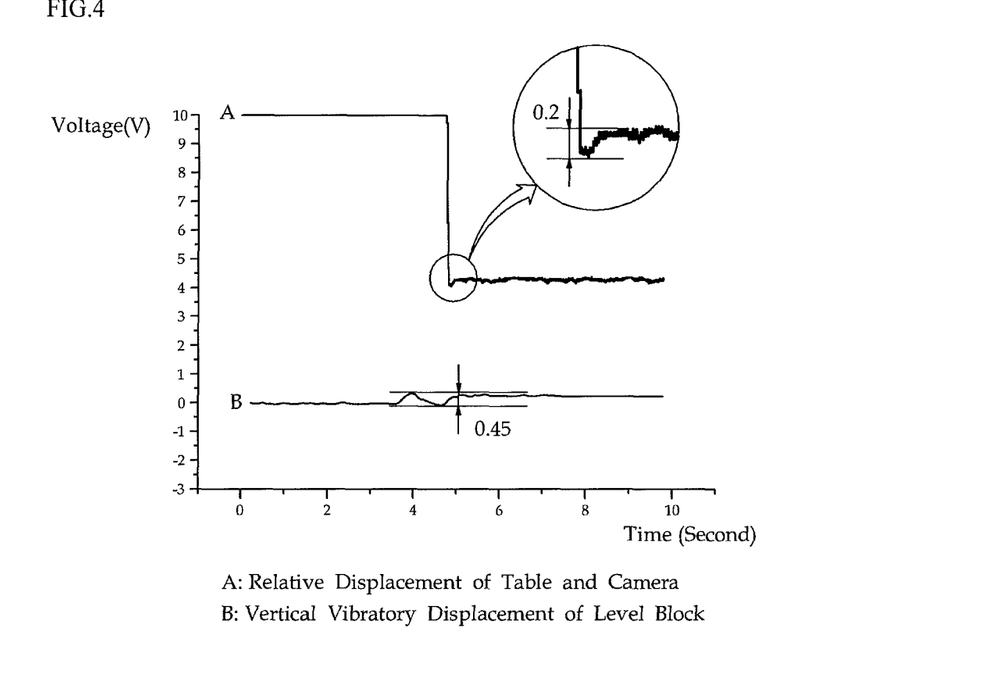
FIG. 4 is a graph representing the relative displacement of a table and a camera and the vertical vibratory displacement of a level block in one embodiment the present vision inspection system, both of which are measured by moving the table and the camera toward each other.
Figure 5:
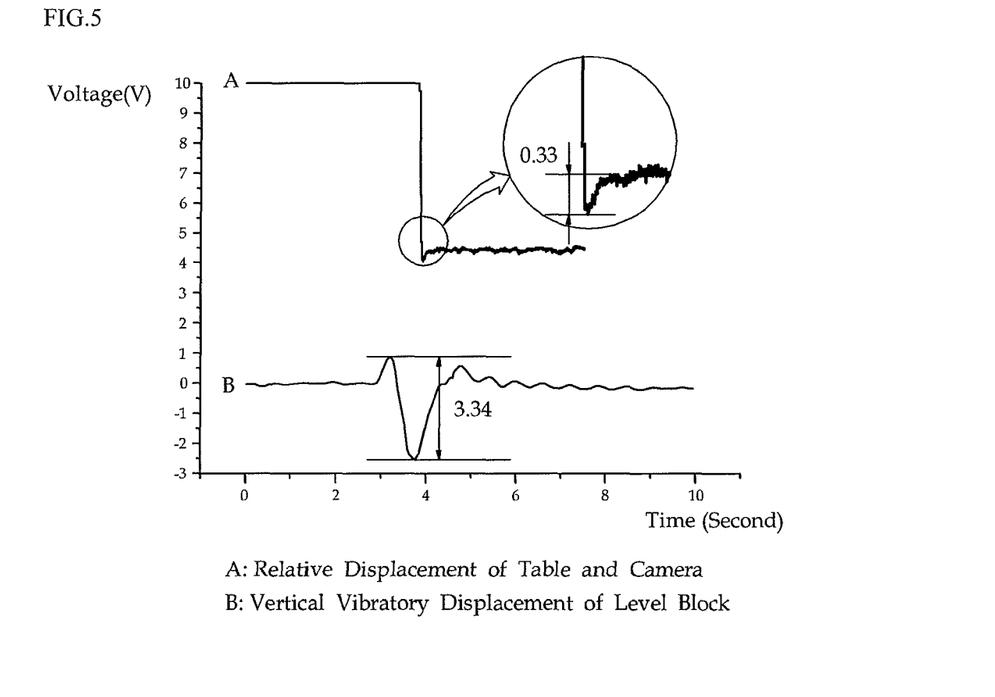
FIG. 5 is a graph representing the relative displacement of a table and a camera and the vertical vibratory displacement of a level block in one embodiment the present vision inspection system, both of which are measured by fixing the table and moving the camera toward the table.

Referring to FIG. 4, the voltage difference corresponding to the relative displacement of the table 32 and the cameras 40 is equal to 0.2V and the voltage difference corresponding to the vertical vibratory displacement of the level block 20 is equal to 0.45V in the experiment of the Example. Turning to FIG. 5, the voltage difference corresponding to the relative displacement of the table 32 and the cameras 40 is equal to 0.33V and the voltage difference corresponding to the vertical vibratory displacement of the level block 20 is equal to 3.34V in the experiment of the Comparative Example.

It can be seen that the voltage difference corresponding to the vertical vibratory displacement of the level block 20 obtained in the experiment of the Example is 2.89V smaller than that obtained in the Comparative Example and further that the voltage difference corresponding to the relative displacement of the table 32 and the cameras 40 obtained in the experiment of the Example is 0.25V smaller than that obtained in the Comparative Example. This means that, as compared to the experiment of the Comparative Example, the vibration of the table 32 and the cameras 40 is sharply reduced in the experiment of the Example.

If the workpiece 2 and the cameras 40 are stopped in an inspection position, the cameras 40 take the images of the workpiece 2 to acquire image data (S22). Since the table 32 and the carriage 54 of the vision inspection system 10 are moved toward each other to thereby reduce the vibration of the level block 20, the table 32 and the cameras 40, it becomes possible to greatly enhance the reliability of the image data acquired by the cameras 40. Furthermore, owing to the fact that the table 32 and the carriage 54 of the vision inspection system 10 are moved toward each other, it is possible to greatly shorten the inspection time of the workpiece 2 as compared to a case that only the carriage 54 is caused to move.

Finally, the computer 60 processes the image data of the workpiece 2 inputted from the cameras 40 using an image processing program (S24). By use of the image processing program stored in the computer 60, inspection is performed to find out defects of the workpiece 2 and then to assort the workpiece 2 into an accepted product and a rejected product. The results of inspection of the workpiece 2 are displayed on the monitor 62. If the inspection of the workpiece 2 is completed, the computer 60 controls the operation of the first transfer device 30 and the second transfer device 50 so that the table 32 and the carriage 54 can be returned back to their original positions.

As described hereinabove, the vision inspection system and the workpiece inspection method described above, the image data is acquired by allowing the first transfer device and the second transfer device to simultaneously move the workpiece and the cameras toward each other. This helps minimize the torque acting in the vision inspection system as a whole, thereby preventing generation of vibration and greatly enhancing the reliability of the image data obtained. It is also possible to sharply reduce the time required in inspecting the workpiece.

The present disclosure is not limited to the embodiments set forth hereinabove. It will be understood by those skilled in the art that various changes and modifications may be made without departing from the scope of the invention defined in the claims.

What is claimed is:

1. A method of obtaining an image of an object, the method comprising:
    moving an object in a first direction;
    moving a camera in a second direction opposite to the first direction while the object is moving;
    capturing at least one image of the object using the camera when the camera and the object are aligned with each other for capturing the at least one image; and
    sending the at least one image of the object to a computing device.

2. The method of claim 1, wherein moving of the camera is controlled such that a first torque generated by moving of the camera substantially compensates a second torque generated by moving of the object.

3. The method of claim 2, further comprising controlling acceleration or deceleration of the object during moving.

4. The method of claim 2, further comprising controlling acceleration or deceleration of the camera during moving.

5. The method of claim 2, further comprising controlling acceleration or deceleration of at least one of the object and the camera during moving thereof, wherein the first torque is proportional to a first distance between the camera and a reference point in a third direction perpendicular to the first direction and the second torque is proportional to a second distance between the object and the reference point in the third direction.

6. The method of claim 1, wherein capturing the at least one image of the object occurs when the camera and the object are stopped after moving opposite directions.

7. The method of claim 1, wherein capturing the at least one image of the object occurs when the camera and the object are aligned with each other.

8. The method of claim 1, wherein the object comprises a flat panel display device.

9. The method of claim 1, further comprising identifying the object from the at least one image.

10. The method of claim 1, further comprising inspecting the object on the at least one image.

11. The method of claim 10, further comprising determining whether to accept or reject the object based on the inspection.

12. A inspection system comprising:
    a table slidable in a first direction and configured to place an object on;

a camera slidable in a second direction opposite to the first direction and configured to capture images of the object; and a computing device configured to process at least one image of the object captured by the camera and to identify a defect on the object.

13. The system of claim 12, wherein the system is configured so as to control sliding of the table and the camera in a manner that a torque generated by sliding of the camera substantially compensates a torque generated by sliding of the table.

14. The system of claim 12, wherein the system further comprises a level block supporting the table and the camera.

15. The system of claim 14, wherein the table is slidable on an upper surface of the level block straight in the first direction.

16. The system of claim 14, wherein the camera is slidable on the upper surface of the level block straight in the second direction.

17. The system of claim 12, wherein the system further comprises a plurality of base isolators for supporting the level block.

18. The system of claim 12, wherein the system comprises a plurality of cameras with each camera configured to capture at least one image of a portion of the object.

* * * * *